(12) United States Patent
Schell

(10) Patent No.: US 6,701,191 B2
(45) Date of Patent: Mar. 2, 2004

(54) LEAD HAVING COMPOSITE TUBING

(75) Inventor: Jon Schell, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/870,369

(22) Filed: May 30, 2001

(65) Prior Publication Data

US 2002/0183821 A1 Dec. 5, 2002

(51) Int. Cl.$^7$ .................................................. A61F 7/00
(52) U.S. Cl. ................................................... 607/122
(58) Field of Search ............................. 607/116–138; 600/373; 504/527

(56) References Cited

U.S. PATENT DOCUMENTS

| | | | |
|---|---|---|---|
| 4,295,270 A | 10/1981 | Cammarata | 29/828 |
| 4,452,254 A | 6/1984 | Goldberg et al. | 128/785 |
| 4,547,193 A | 10/1985 | Rydell | 604/282 |
| 4,559,951 A | 12/1985 | Dahl et al. | 128/642 |
| 4,699,157 A | 10/1987 | Shonk | 128/786 |
| 5,005,587 A | 4/1991 | Scott | 128/786 |
| 5,014,721 A | 5/1991 | Hirschberg | 128/786 |
| 5,057,092 A | * 10/1991 | Webster, Jr. | 138/123 |
| 5,181,920 A | 1/1993 | Mueller et al. | 606/159 |
| 5,336,254 A | 8/1994 | Brennen et al. | 607/129 |
| 5,397,304 A | 3/1995 | Truckai | 604/95 |
| 5,569,220 A | * 10/1996 | Webster, Jr. | 138/125 |
| 5,591,142 A | * 1/1997 | Van Erp | 604/264 |
| 5,628,774 A | 5/1997 | Helland et al. | 607/116 |
| 5,662,621 A | 9/1997 | Lafontaine | 604/281 |
| 5,674,272 A | 10/1997 | Bush et al. | 607/122 |
| 5,680,860 A | 10/1997 | Imran | 128/642 |
| 5,755,762 A | 5/1998 | Bush | 607/122 |
| 5,814,090 A | 9/1998 | Latterell et al. | 607/36 |
| 5,843,076 A | 12/1998 | Webster, Jr. et al. | 606/41 D |
| 5,843,149 A | 12/1998 | Ebert et al. | 607/116 |
| 5,851,226 A | 12/1998 | Skubitz et al. | 607/126 |
| 5,865,791 A | 2/1999 | Whayne et al. | 604/49 |
| 5,882,346 A | 3/1999 | Pomeranz et al. | 604/280 |
| 5,891,135 A | 4/1999 | Jackson et al. | 606/41 |
| 5,891,136 A | 4/1999 | McGee et al. | 606/41 |
| 5,921,982 A | 7/1999 | Lesh et al. | 606/41 |
| 5,925,038 A | 7/1999 | Panescu et al. | 606/41 |
| 5,931,862 A | 8/1999 | Carson | 607/120 |
| 5,984,917 A | 11/1999 | Fleischman et al. | 606/32 |
| 6,051,017 A | 4/2000 | Loeb et al. | 607/1 |
| 6,055,457 A | 4/2000 | Bonner | 607/126 |
| 6,083,216 A | 7/2000 | Fischer, Sr. | 604/530 |
| 6,122,552 A | 9/2000 | Tockman et al. | 607/116 |
| 6,132,438 A | 10/2000 | Fleischman et al. | 606/139 |
| 6,181,965 B1 | 1/2001 | Loeb et al. | 607/3 |
| 6,213,995 B1 | * 4/2001 | Steen et al. | 604/527 |
| 6,217,528 B1 | 4/2001 | Koblish et al. | 600/585 |
| 6,477,428 B1 | * 11/2002 | Skinner et al. | 607/122 |

* cited by examiner

*Primary Examiner*—Mark Bockelman
(74) *Attorney, Agent, or Firm*—Schwegman, Lundberg, Woessner & Kluth, P.A.

(57) ABSTRACT

A lead assembly includes a flexible lead body which extends from a proximal end to a distal end, the lead body includes one or more conductors. The lead assembly further includes an electrode assembly, and at least one coating of insulative material coated directly on at least one conductor.

33 Claims, 5 Drawing Sheets

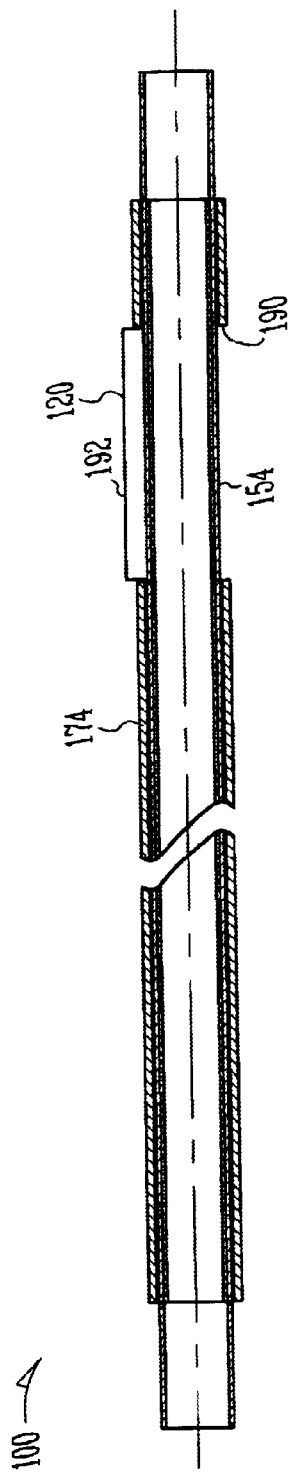
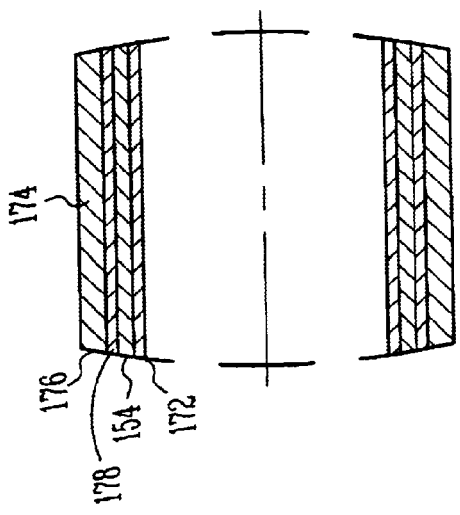
Fig.4
Fig.3

LEAD HAVING COMPOSITE TUBING

RELATED APPLICATIONS

This application is related to U.S. Patent Application entitled "TORQUE MECHANISM AND METHOD FOR ENDOCARDIAL LEADS," filed on May 30, 2001 as Ser. No. 09/870,126 now U.S. Pat. No. 6,606,522, and to U.S. patent application Ser. No. 09/292,715, filed on Apr. 15, 1999, entitled "STEERABLE CORONARY SINUS DEFIBRILLATION LEAD" now U.S. Pat. No. 6,445,958, each of which are incorporated by reference herein.

TECHNICAL FIELD

The present invention relates generally to leads for stimulating or monitoring tissue. More particularly, it pertains to a lead having composite tubing.

BACKGROUND

Leads implanted in or about the heart have been used to reverse certain life threatening arrhythmias, or to stimulate contraction of the heart. Electrical energy is applied to the heart via the leads to return the heart to normal rhythm. Leads have also been used to sense in the atrium or ventricle of the heart and to deliver pacing pulses to the atrium or ventricle.

Cardiac pacing may be performed by the transvenous method or by leads implanted directly onto the epicardium. Permanent transvenous pacing is performed using a lead positioned within one or more chambers of the heart. One or more leads may be positioned in the ventricle or in the atrium through a subclavian vein, and the lead terminal pins are attached to a pacemaker which is implanted subcutaneously.

The lead includes a conductor, such as a coiled conductor, to conduct energy from the pacemaker to the heart, and also signals received from the heart. The lead further includes outer insulation to insulate the conductor. Currently, providing the lead with insulation is done by stringing silicone tubing over the lead. Stringing involves the use of chemicals which swell the silicone tubing, so that the coiled conductor can be pulled through the tubing. As the chemicals evaporate, the tubing contracts around the conductor. Stringing is a complicated manufacturing process which also can result in axial gaps between the conductor and the insulative tubing. The gaps contribute to the outer diameter of the lead.

Accordingly, there is a need for a lead which allows for a less complex manufacturing process and improved insulation. What is also needed is a lead having a smaller outer diameter.

SUMMARY OF THE INVENTION

A lead assembly includes a flexible lead body which extends from a proximal end to a distal end, the lead body includes one or more conductors. The lead body includes an outer coating of composite insulative material. The lead assembly further includes an electrode assembly, and the outer coating of composite material is coated directly on at least one conductor.

Several options for the lead assembly are as follows. For instance, in one option, one or more conductors include a first conductor and a second conductor, and at least one coating is coated between the first conductor and the second conductor. In another option, at least one of the conductors comprises a braided conductor. In yet another option, the conductor extends from a first end to a second end and has an intermediate section therebetween, and a portion of the intermediate section has an exposed, non-coated area. The lead assembly, in another option, further includes one or more electrodes electrically coupled with the exposed non-coated area. In another option, the composite coating comprises a first coating and a second coating coated over the first coating.

In another embodiment, a lead assembly includes a flexible lead body which extends from a proximal end to a distal end, the lead body includes one or more conductors, for instance a first conductor and a second conductor. The flexible lead body comprises a first coating disposed directly on a first conductor. The lead assembly further includes an electrode assembly. In addition, at least one second coating of insulative material is coated directly on a second conductor, where the second coating is coated between the first conductor and the second conductor.

Several options for the lead assembly are as follows. For instance, the first conductor, in one option, comprises a braided conductor. In another option, the first conductor extends from a first end to a second end and has an intermediate section therebetween, and a portion of the intermediate section has an exposed, non-coated area, and optionally one or more electrodes are mechanically coupled with the exposed non-coated area. In yet another option, the first conductor comprises a means for extending and retracting the electrode assembly. The lead assembly includes, in another option, a third coating of insulative material coated directly on the first coating of insulative material.

In another embodiment, a lead assembly includes a flexible lead body which extends from a proximal end to a distal end, the lead body includes one or more conductors, where at least one conductor comprises a braided conductor configured to conduct electrical signals. The lead assembly further includes at least one electrode electrically coupled with at least one conductor, and at least one coating of insulation coated directly on the braided conductor.

Several options for the lead assembly are as follows. For instance, in one option, a portion of the at least one coating is removed from the braided conductor to reveal an exposed portion of the braided conductor, and at least one electrode is electrically and mechanically coupled with the exposed portion of the braided conductor. In another option, the braided conductor is rotatable to extend and/or retract at least one electrode. In yet another option, the lead assembly further includes a second coating of insulation coated between the braided conductor and a second conductor, and the second coating is coated directly on the second conductor. Alternatively, the lead assembly further includes an outer coating of composite insulative coating, for example a first coating and a second coating coated directly on the first coating.

In another embodiment, a method comprises providing a first conductor, forming an outer composite lead body over the first conductor, which includes coating composite insulative material directly on a first conductor. The method further includes coupling at least one electrode with the first conductor.

Several options for the method are as follows. For instance, in one option, the method further includes braiding multiple conductors to form the first conductor, and optionally includes rotating the first braided conductor, and extending the at least one electrode. In another option, the method further includes stripping insulative material from a portion of the first conductor, and exposing a portion of the first conductor, and optionally further mechanically and electrically coupling an electrode to the exposed portion of the first conductor. Alternatively, in another option, the method further includes providing a second conductor, and coating a second coating directly on the second conductor.

In another embodiment, a method comprises providing a first conductor for a lead, the first conductor extending from a proximal end to a distal end and having an inner diameter surface and an outer diameter surface. The method further includes coating the outer diameter surface of the first conductor with an insulative coating, including leaving the inner diameter surface uncoated. A second conductor is provided which is coaxial with the first conductor, where the first conductor has a different outer diameter than the second conductor. The method further includes coupling at least one electrode with the first conductor, and coupling the proximal end of the first conductor with an energy source configured to stimulate tissue.

Several options for the method are as follows. For instance, in one option, the method further includes rotating the conductor, and extending the at least one electrode away from the lead. In another option, the method further includes stripping insulative material from a portion of the first conductor, and exposing a portion of the first conductor, and optionally further mechanically and electrically coupling an electrode to the exposed portion of the first conductor. Alternatively, in another option, coating the first conductor includes forming an outer lead body of composite insulative material. In yet another option, the method further includes coating an outer diameter of the second conductor with insulative material.

The lead provides for a smaller lead body diameter due to the elimination of gaps, and tolerance stack-up of the assembly. The lead allows for the ability to start and stop tubing to allow for transition areas of the outer insulation, allowing for the device to have an isodiametric shape. Furthermore, the braided conductors have multiple intersections which offer improved flex fatigue properties. A further benefit is that the anode and cathode are not co-radial, the cathode is suitable for use as a driving mechanism for an extendable or retractable positive fixation lead.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 3 is a cross-section of a portion of a lead assembly constructed in accordance with one embodiment.

FIG. 4 is a cross-section of a lead assembly constructed in accordance with another embodiment.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
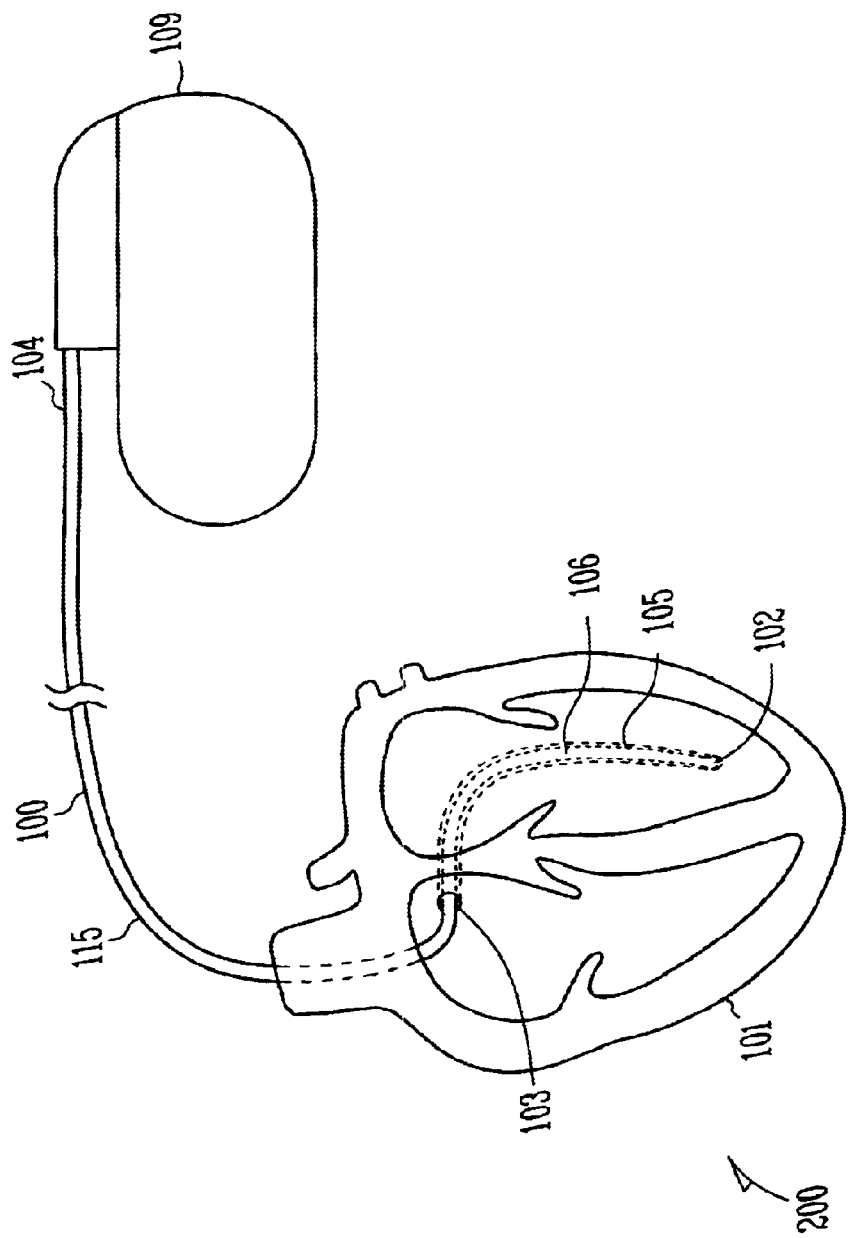
FIG. 1 illustrates a system for monitoring and stimulating the heart constructed in accordance with one embodiment.

FIG. 1 illustrates a system 200 for delivering electrical pulses to stimulate a heart 101 and/or for receiving electrical pulses to monitor the heart 101. The system 200 includes a pulse generator and signal sensor 109 and a lead 100. The lead 100 extends from a distal end 102 to a proximal end 104, and has an intermediate portion 106 therebetween. The distal end 102 is adapted for implantation within the heart of a patient and the proximal end 104 has a terminal connector which electrically connects the various electrodes and conductors within the lead body 115 to a pulse generator and signal sensor 109. The pulse generator and signal sensor 109 contains electronics to sense various electrical signals of the heart and also produce current pulses for delivery to the heart 101. The pulse generator and signal sensor 109 is implanted pectorally, abdominally, or elsewhere within the patient.

The lead 100 includes a lead body 115, for instance a flexible lead body 115, at least one elongate conductor 150 (FIGS. 2 and 3) contained within the lead body 115, and at least one electrode 120 (FIG. 4) coupled with the lead 100. The lead body 115, as further described below, includes an elongate body formed of, for example, at least one polymer such as a medical grade silicone rubber for translumenal insertion and access within a living organism such as a patient. In one option, the lead body 115 is tubular and has an outer diameter that is small enough for translumenal insertion into the coronary sinus 103 and/or great cardiac vein 105.

Figure 2:
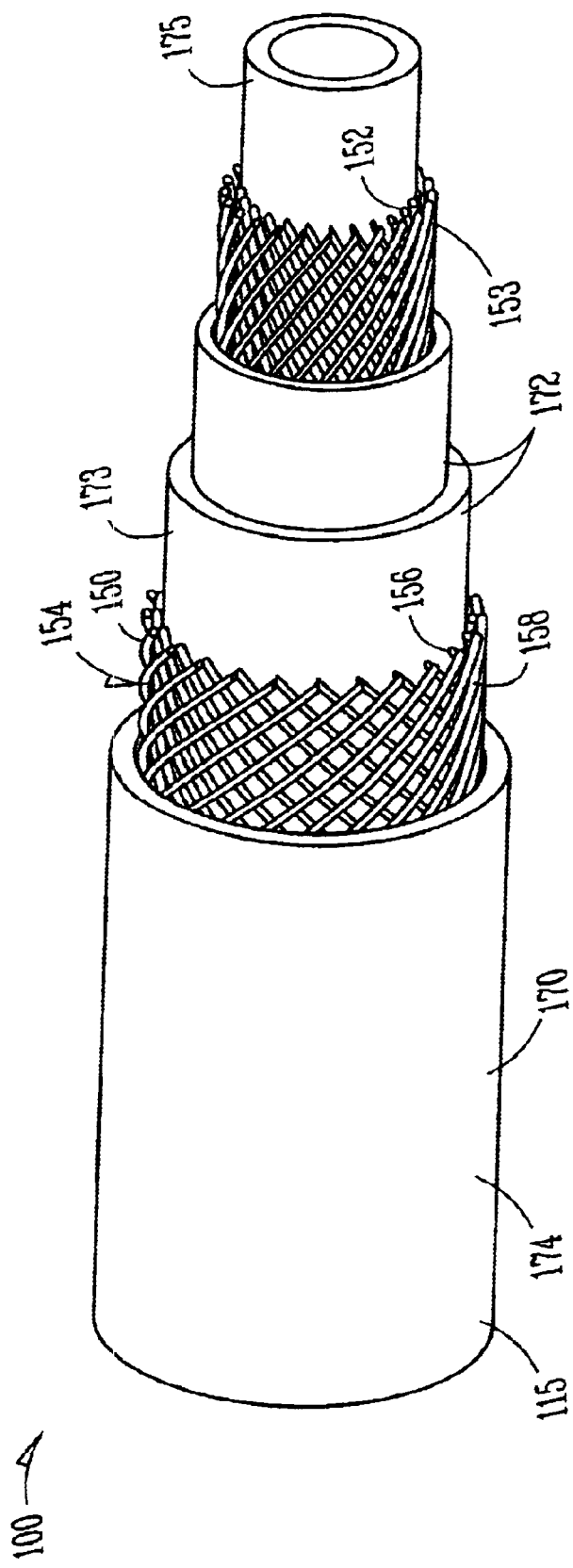
FIG. 2 is a perspective view of a portion of a lead assembly constructed in accordance with one embodiment.

The at least one electrode 120 is electrically coupled with the elongate conductor 150 (FIGS. 2 and 3). Optionally, the elongate conductor 150 comprises a coiled conductor and defines a lumen therein and thereby is adapted to receive a stiffening stylet that extends through the length of the lead 100.

The stylet is used to stiffen the lead 100, and is manipulated to facilitate the insertion of the lead 100 into and through a vein and through an intracardiac valve to advance the distal end 102 of the lead 100 into, for example, the ventricle of the heart 101. Optionally, a stylet knob is coupled with the stylet for rotating the stylet, advancing the conductor into tissue of the heart, and for manipulating the lead 100. Alternatively, the elongate conductor 150 comprises other forms of conductors, such as a cable conductor, or a braided conductor as further discussed below.

FIG. 2 illustrates a portion of the lead shown in FIG. 1, including the lead 100, and/or the lead 100 and the pulse generator and signal sensor 109 (FIG. 1). The lead 100, in one option, is used to chronically stimulate the heart 101 (FIG. 1), such that the lead 100 is implanted on or about the heart 101 (FIG. 1) for long periods of time. As mentioned above, the lead body 115 includes a covering of insulation, and includes at least one elongate conductor 150. In one option, the elongate conductor 150 extends substantially along the entire length between the distal end 102 (FIG. 1) and the proximal end 104 (FIG. 1) of the lead 100. The elongate conductor 150, in one option, includes a first inner conductor 152 and a second conductor 154. In another option, the first inner conductor 152 comprises a cathode of the system 200 (FIG. 1), and the second conductor 154 comprises an anode of the system 200 (FIG. 1).

The first inner conductor 152, in one option, is co-axial but not co-radial with the second conductor 154. For example, the first inner conductor 152 is disposed within the second conductor 154. The first inner conductor 152 and/or the second conductor 154 comprises braided material, as further discussed below. An inner layer of insulation 172 is disposed between the first inner conductor and the second conductor 154. The inner layer of insulation 172 is in addition to the lead body 115 which includes at least one outer layer of insulation 170. Optionally, a second inner layer of insulation 175 is disposed within the first inner conductor 152.

The outer layer of insulation 170, in one option, is disposed adjacent to the second conductor 154. The second conductor 154 is defined in part by an inner surface 156 and an outer surface 158. In one option, the outer layer of insulation 170 is disposed directly on the outer surface 158 of the second conductor 154. For instance, the outer layer of insulation 170 is coated directly on the outer surface 158 of the second conductor 154 to form a coating. Examples of coating process include, but are not limited to, spray coating, dipping, brush coating. The coating, in one option, comprises a composite coating 174 formed of two or more insulative materials. It should be noted that more than two layers of insulative materials could be utilized. In one example, as shown in FIG. 3, the composite coating 174 comprises a first outer coating 176 and a second outer coating 178 of material. In another option, the second outer coating 178 is coated directly on the first outer coating 176. In one option, one of the coatings comprises PTFE, and the other coating comprises polyurethane. Other suitable materials for use with the composite coating 174 include, but are not limited to, silicone or elastomeric material.

Referring again to FIG. 2, the inner layer of insulation 172 is disposed directly on the first inner conductor 152. It should be noted that more than one inner layer of insulation could be incorporated into the lead. The first inner conductor 152 is defined in part by an inner surface 151 and an outer surface 153. As shown in FIG. 2, the inner layer of insulation 172 is disposed directly on the outer surface 153 of the first inner conductor 152. For instance, the inner layer of insulation 172 is coated directly on the outer surface 153 of the first inner conductor 152. Optionally, the inner layer of insulation 172 comprises a composite coating. Suitable materials for the inner layer of insulation 172 include, but are not limited to, PTFE, ETFE, or polyimide.

In one example of the lead 100, the inner layer of insulation 172 comprises a layer which is a minimum of 2 mm thickness, for example, of PTFE. The second conductor 154 comprises a braided conductor, for example having a 3 mm thickness. The first outer coating 176 comprises a layer which is a minimum of 2 mm thickness, for example, of PTFE, and the second outer coating 178 comprises polyurethane.

Referring to FIG. 4, the lead 100 is shown with a composite outer coating 174 coated directly on the conductor 154. Optionally, a portion 190 of the coating 174 is removed at an intermediate section of the lead 100, and the conductor 154 is exposed. For example, the portion 190 is removed by mechanical stripping, laser stripping, or masking during the coating process. In yet another option, one or more electrodes 192 are electrically and optionally mechanically coupled with the exposed portion 190. For example, the one or more electrodes 192 is welded or swaged with the conductor 154. In another example, the one or more electrodes 192 is crimped or bonded with the conductor 154. The exposed portion 190 allows for the outer body of the lead 100 to be made isodiametrically, which allows for the lead 100 to be more easily inserted into a patient.

Figure 5:
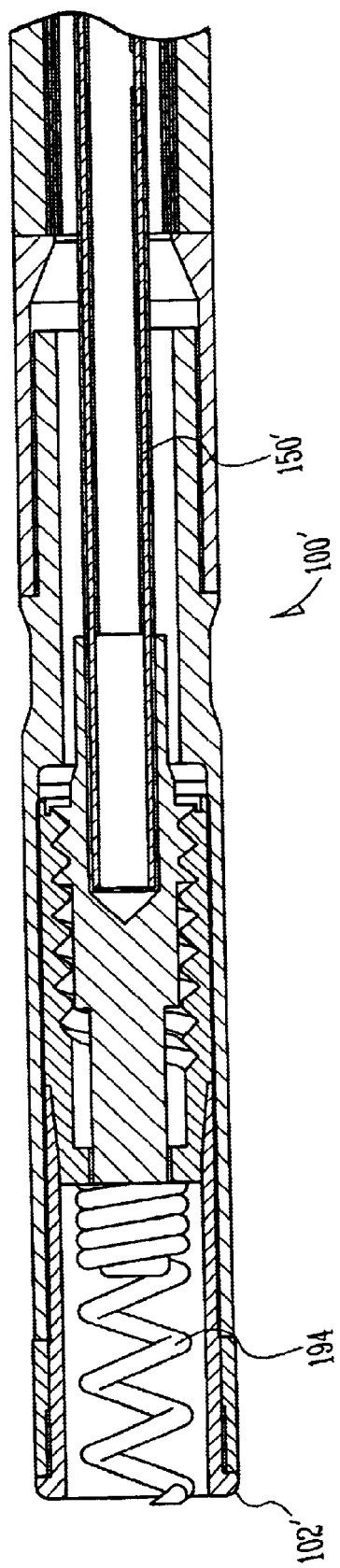
FIG. 5 is a cross-section of a lead assembly constructed in accordance with another embodiment.

FIG. 5 illustrates a distal end 102' of one option of the lead 100'. The lead 100' includes an active fixation device 194 which allows for the distal end 102' of the lead 100' to be fixated with tissue. In one option, the active fixation device 194 comprises a sharpened helical tip. In one option, the active fixation device 194 is mechanically coupled directly or indirectly with the conductor 150' such that rotating the conductor 150' rotates the active fixation device 194. In one option, the conductor 150' comprises a braided conductor, as discussed above. In another option, the conductor 150' comprises a coated braided conductor, as discussed above. The conductor 150' is, in one example, welded or crimped with the active fixation device 194. The conductor 150' comprises a non-coiled conductor of sufficient rigidity to transmit torque provided at the proximal end of the lead to the active fixation device 194 at the distal end of the lead.

Figure 6:
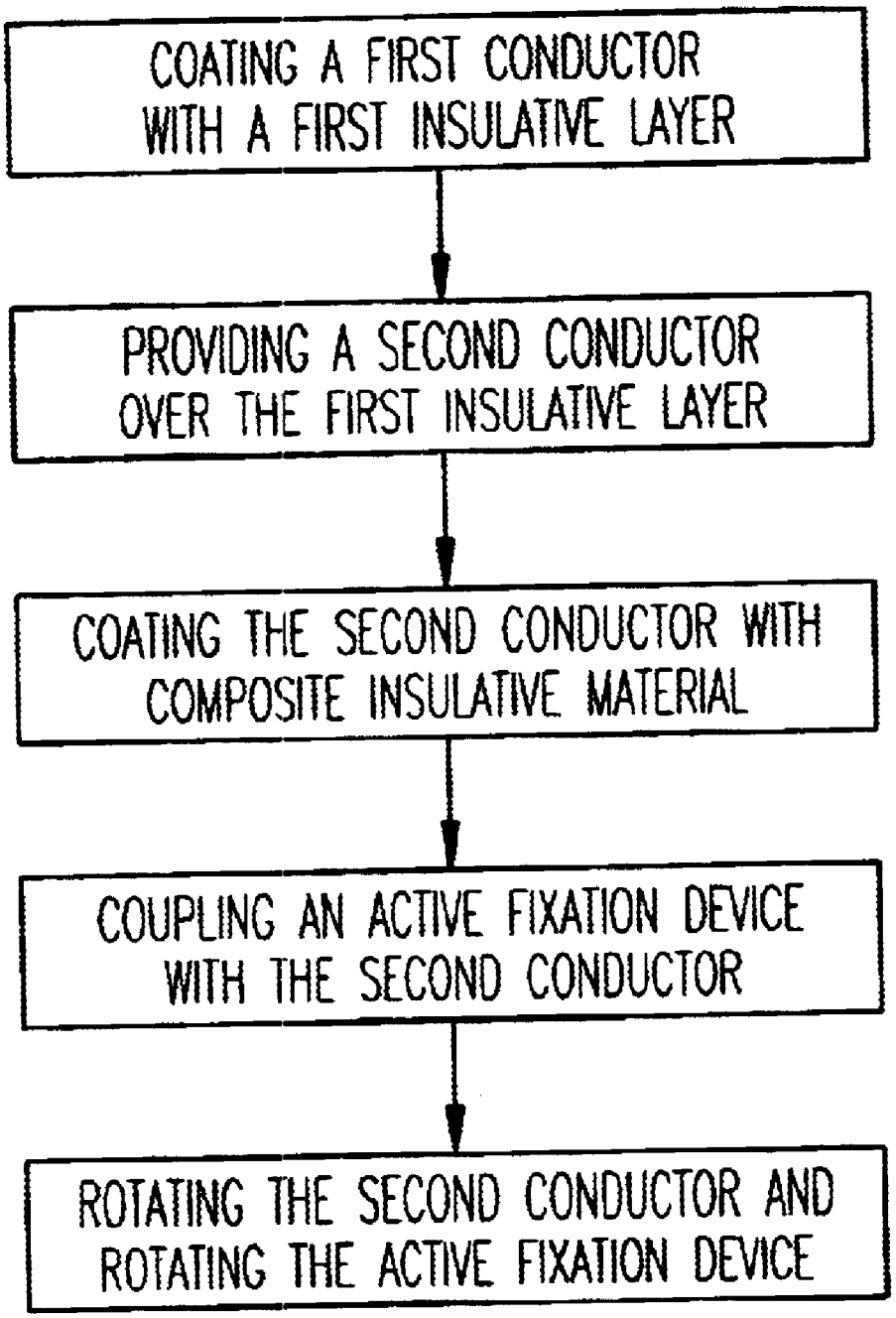
FIG. 6 is a block diagram illustrating a method in accordance with another embodiment.

Referring to FIG. 6, a block diagram is shown illustrating a method which includes coating a first conductor with a first insulative layer, providing a second conductor over the first insulative layer, and coating the second conductor with composite insulative material. In one option, the second conductor is provided directly on the first insulative layer, and/or the first conductor is slidably received within the second conductor. The method optionally includes coupling an active fixation device with the second conductor, and rotating the second conductor and rotating the active fixation device.

In another embodiment, a method comprises providing a first conductor, forming an outer composite lead body over the first conductor, which includes coating composite insulative material directly on a first conductor. The method further includes coupling at least one electrode with the first conductor. For example, a ring electrode is slipped over the conductor and is electrically and optionally mechanically coupled with the conductor.

Several options for the method are as follows. For instance, in one option, the method further includes braiding multiple conductors to form the first conductor, and optionally includes rotating the first braided conductor, and extending the at least one electrode. In another option, the method further includes stripping insulative material from a portion of the first conductor, and exposing a portion of the first conductor, and optionally further mechanically and electrically coupling an electrode to the exposed portion of the first conductor. Alternatively, in another option, the method further includes providing a second conductor, and coating a second coating directly on the second conductor.

In another embodiment, a method comprises providing a first conductor for a lead, the first conductor extending from a proximal end to a distal end and having an inner diameter surface and an outer diameter surface. The method further includes coating the outer diameter surface of the first conductor with an insulative coating, including leaving the inner diameter surface uncoated. A second conductor is provided which is coaxial with the first conductor, where the first conductor has a different outer diameter than the second conductor. The method further includes coupling at least one electrode with the first conductor, and coupling the proximal end of the first conductor with an energy source configured to stimulate tissue.

Several options for the method are as follows. For instance, in one option, the method further includes rotating the conductor, and extending the at least one electrode away from the lead. In another option, the method further includes stripping insulative material from a portion of the first conductor, and exposing a portion of the first conductor, and optionally further mechanically and electrically coupling an electrode to the exposed portion of the first conductor. Alternatively, in another option, coating the first conductor includes forming an outer lead body of composite insulative material. In yet another option, the method further includes coating an outer diameter of the second conductor with insulative material.

Advantageously, the above described lead provides for a smaller lead body diameter due to the elimination of gaps, and tolerance stack-up of the assembly. Since the insulative material is coated, rather than formed of tubing, the outer dimension of the lead can be made smaller, and the lead can be made more cost effectively. Furthermore, the coating of insulative material does not involve the complex manufacturing processes involved with tubing insulation. In addition, the above described device allows for the ability to start and stop tubing to allow for transition areas of the outer insulation, allowing for the device to have an isodiametric shape. Furthermore, the braided conductors have multiple intersections which offer improved flex fatigue properties. A further benefit is that the anode and cathode are not co-radial, the cathode is suitable for use as a driving mechanism for an extendable or retractable positive fixation lead.

It is to be understood that the above description is intended to be illustrative, and not restrictive. For instance, the leads described above include, but are not limited to, tachy, brady, or coronary sinus leads. It should be noted that features of the various above-described embodiments may be interchanged to form additional combinations. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A lead assembly comprising:
   a flexible lead body extending from a proximal end to a distal end, the lead body including one or more conductors disposed therein;
   the lead body including an outer coating of composite insulative material;
   an electrode assembly including at least one electrode electrically coupled with at least one conductor;
   the outer coating of composite insulative material coated directly on at least one conductor; and
   wherein the one or more conductors includes a first conductor disposed within a second conductor, and at least one coating is coated between the first conductor and the second conductor, and a layer of insulation is disposed within the first conductor.

2. The lead assembly as recited in claim 1, wherein the second conductor comprises a braided conductor.

3. The lead assembly as recited in claim 1, wherein the first conductor comprises a braided conductor.

4. The lead assembly as recited in claim 1, wherein one of the conductors extends from a first end to a second end and has an intermediate section therebetween, and a portion of the intermediate section has an exposed, non-coated area.

5. The lead assembly as recited in claim 4, further comprising one or more electrodes electrically coupled with the exposed non-coated area.

6. The lead assembly as recited in claim 1, wherein the outer coating of composite insulative material comprises a first coating and a second coating coated over the first coating.

7. The lead assembly as recited in claim 1, wherein the at least one coating between the first conductor and the second conductor is a composite insulative material.

8. A lead assembly comprising:
   a flexible lead body extending from a proximal end to a distal end, the lead body including one or more conductors disposed therein, the flexible lead body comprising a first coating disposed directly on a first conductor,
   an electrode assembly including at least one electrode electrically coupled with at least one conductor;
   at least one second coating of insulative material coated directly on a second conductor the second conductor disposed within the first conductor, the at least one second coating is coated between the first conductor and the second conductor, and
   wherein the first conductor extends from a first end to a second end and has an intermediate section therebetween, and a portion of the intermediate section has an exposed, non-coated area between two coated areas.

9. The lead assembly as recited in claim 8, wherein the first conductor comprises a braided conductor.

10. The lead assembly as recited in claim 8, wherein the second conductor comprises a braided conductor.

11. The lead assembly as recited in claim 8, further comprising one or more electrodes mechanically coupled with the exposed non-coated area.

12. The lead assembly as recited in claim 8, wherein the first conductor comprises a means for extending and retracting the electrode assembly.

13. The lead assembly as recited in claim 8, further comprising a third coating of insulative material coated directly on the first coating of insulative material.

14. The lead assembly as recited in claim 13, wherein the first coating is formed of a first material, and the third coating is formed of a second material, and the first material is different than the second material.

15. A lead assembly comprising:
   a lead body extending from a proximal end to a distal end, the lead body including a first conductor disposed therein,
   an electrode assembly including at least one electrode electrically coupled with the conductor;
   a first coating of insulation coated directly on the first conductor, the first coating made from a first material;
   a second coating of insulation coated directly on the first coating, the second coating made from a second material;
   a second conductor disposed within the first conductor;
   a third coating of insulation coated directly on the second conductor, the third coating made from one material; and
   a fourth coating of insulation coated directly on the third coating, the fourth coating made from another material, wherein said third and fourth coatings are disposed within said coated first conductor.

16. The lead assembly as recited in claim 15, wherein a portion of the of the first coating and the second coating are removed from the first conductor to reveal an exposed portion of the first conductor, and at least one electrode is electrically and mechanically coupled with the exposed portion of the first conductor.

17. The lead assembly as recited in claim 15, wherein the second conductor is rotatable to extend and/or retract at least one electrode.

18. The lead assembly as recited in claim 15, wherein the first conductor is a braided conductor and the second conductor is a braided conductor.

19. The lead assembly as recited in claim 15, wherein the second coating is an outer coating of the lead body.

20. The lead assembly as recited in claim 19, wherein the first coating and the second coating form a composite coating.

21. A method comprising:
   providing a first conductor;
   forming an outer composite lead body over the first conductor including coating composite insulative material directly on the first conductor;
   coating composite insulative material directly on a second conductor; disposing the second conductor within the first conductor such that the second conductor composite coating is disposed within said coated first conductor; and
   coupling at least one electrode with the first conductor.

22. The method as recited in claim 21, further comprising braiding multiple conductors to form the first conductor.

23. The method as recited in claim 21, further comprising rotating the second conductor, to extend the at least one electrode away from the outer composite lead body.

24. The method as recited in claim 21, further comprising stripping insulative material from a portion of the first conductor, and exposing a portion of the first conductor.

25. The method as recited in claim 24, further comprising mechanically and electrically coupling an electrode to the exposed portion of the first conductor.

26. The method as recited in claim 21, further comprising braiding multiple conductors to form the second conductor.

27. The method as recited in claim 21, wherein forming the outer composite lead body includes coating a first layer of a first material directly on the first conductor, and coating a second layer of a second material directly on the first layer of first material.

28. A method comprising:
   providing a first conductor for a lead, the first conductor extending from a proximal end to a distal end and having an inner diameter surface and an outer diameter surface;
   coating the outer diameter surface of the first conductor with an insulative coating, including leaving the inner diameter surface uncoated;
   providing a second conductor coaxial with the first conductor, where the first conductor has a different outer diameter than the second conductor;
   coupling at least one electrode with the first conductor; and
   coupling the proximal end of the first conductor with an energy source configured to stimulate tissue.

29. The method as recited in claim 28, further comprising rotating the coated first conductor, and extending the at least one electrode away from the lead.

30. The method as recited in claim 28, further comprising stripping insulative material from a portion of the first conductor, and exposing a portion of the first conductor.

31. The method as recited in claim 30, further comprising mechanically and electrically coupling an electrode to the exposed portion of the first conductor.

32. The method as recited in claim 28, wherein coating the first conductor includes forming an outer lead body of composite insulative material.

33. The method as recited in claim 28, further comprising coating an outer diameter of the second conductor with insulative material.

* * * * *